US012714820B2

(12) United States Patent
Poormand et al.

(10) Patent No.: US 12,714,820 B2
(45) Date of Patent: Aug. 25, 2026

(54) RESUSCITATION CIRCUITS INCORPORATING MICROBIAL FILTERS

(71) Applicant: Flexicare, Inc., Irvine, CA (US)

(72) Inventors: Ghassem Poormand, London (GB); Tudor Norman Thomas, Cardiff (GB)

(73) Assignee: Flexicare, Inc., Irvine, CA (US)

(*) Notice: Subject to any disclaimer, the term of this patent is extended or adjusted under 35 U.S.C. 154(b) by 1206 days.

(21) Appl. No.: 17/689,958

(22) Filed: Mar. 8, 2022

(65) Prior Publication Data

US 2022/0288344 A1 Sep. 15, 2022

Related U.S. Application Data

(60) Provisional application No. 63/158,884, filed on Mar. 9, 2021.

(51) Int. Cl.

*A61M 16/10* (2006.01)
*A61M 16/08* (2006.01)
*A61M 16/20* (2006.01)

(52) U.S. Cl.

CPC .... *A61M 16/1065* (2014.02); *A61M 16/0833* (2014.02); *A61M 16/1055* (2013.01); *A61M 16/201* (2014.02); *A61M 16/0875* (2013.01); *A61M 2205/7509* (2013.01)

(58) Field of Classification Search

CPC .. A61M 16/00; A61M 16/06; A61M 16/0833; A61M 16/0875; A61M 16/1055; A61M 16/1065; A61M 16/201; A61M 16/208; A61M 2205/7509

See application file for complete search history.

(56) References Cited

U.S. PATENT DOCUMENTS

| | | | | |
|---|---|---|---|---|
| 7,980,244 B2 | 7/2011 | Boone et al. | | |
| 2001/0054423 A1* | 12/2001 | Gray | A61M 16/0084 | 128/205.13 |
| 2002/0117173 A1* | 8/2002 | Lynn | A61M 16/0078 | 128/202.28 |
| 2009/0020127 A1* | 1/2009 | Boone | A61N 1/3968 | 128/207.14 |
| 2010/0199991 A1* | 8/2010 | Koledin | A61M 16/107 | 128/205.12 |
| 2011/0083670 A1* | 4/2011 | Walacavage | A61M 16/107 | 128/205.12 |
| 2013/0081616 A1* | 4/2013 | Tatkov | A61M 16/0066 | 128/201.13 |
| 2014/0107518 A1* | 4/2014 | Korneff | A61M 16/1065 | 128/205.13 |
| 2016/0279377 A1 | 9/2016 | DeVries et al. | | |

(Continued)

OTHER PUBLICATIONS

G. Tiliket et al., "A new material for airborne virus filtration," Chemical Engineering Journal 173 (2011), pp. 341-351.

(Continued)

*Primary Examiner* — Joseph D. Boecker

(74) *Attorney, Agent, or Firm* — Robert D. Buyan; Stout, Uxa & Buyan, LLP

(57) ABSTRACT

Devices and methods for resuscitation of a patient wherein inspiratory gas is delivered through a T piece circuit having an exhalation port and a filter located upstream of the exhalation port to remove microbes from exhaled respiratory gas before the respiratory gas exits through the exhalation port.

12 Claims, 5 Drawing Sheets

(56) References Cited

U.S. PATENT DOCUMENTS

| | | | | |
|---|---|---|---|---|
| 2021/0322704 | A1* | 10/2021 | Lin | A61M 16/101 |
| 2022/0273897 | A1* | 9/2022 | Weingart | A61M 16/209 |
| 2023/0191050 | A1* | 6/2023 | Salas | A61M 16/0084<br>128/205.13 |
| 2024/0216623 | A1 | 7/2024 | Newhouse et al. | |

OTHER PUBLICATIONS

Sophie Tribolet et al., "Ventilation devices for neonatal resuscitation at birth: A systematic review and meta-analysis," Resuscitation vol. 183, 2022, pp. 109681-109691.
Daniele Trevisanuto, MD et al., "Devices for Administering Ventilation at Birth: A Systematic Review," Pediatrics vol. 148, No. 1, Jul. 2021.
Khalid Aziz et al., "Part 5: Neonatal Resuscitation. 2020 American Heart Association Guidelines for Cardiopulmonary Resuscitation and Emergency Cardiovascular Care," Circulation vol. 142(suppl 2), 2020, pp. S524-S550.
Emanuela Zannin et al., "Bacterial—viral filters to limit the spread of aerosolized respiratory pathogens during neonatal respiratory support in a pandemic era," Pediatric Research (2021) 89:1322-1325.

* cited by examiner

RESUSCITATION CIRCUITS INCORPORATING MICROBIAL FILTERS

RELATED APPLICATION

This patent application claims priority to U.S. Provisional Patent Application No. 63/158,884 entitled RESUSCITATION CIRCUITS INCORPORATING MICROBIAL FILTERS filed Mar. 9, 2021, the entire disclosure of which is expressly incorporated herein by reference.

FIELD OF THE INVENTION

The present invention relates generally to the fields of medicine and biomedical engineering and more particularly to systems and methods used for ventilating and resuscitating infants and other patients.

BACKGROUND

Pulmonary resuscitation is sometimes performed in hospital as well as pre-hospital settings using various automated and manual devices. For manually controlled resuscitation of certain patients, such as infants and small children, a resuscitator device is connected to one end of a T-piece circuit. A T-piece located at the opposite end of that circuit has a mask or other airway engaging device on one side and an exhalation port on the other side. Inspiratory gas (air, oxygen or oxygen/air mixture) flows continuously from the resuscitator device, through the circuit and out of the exhalation port. When it is desired to deliver inspiratory flow (e.g., an assisted breath) to the patient, an operator places his or her finger over the exhalation port, thereby blocking outflow through the exhalation port and causing the flow of inspiratory gas to flow through the mask or other airway device and into the patient's lungs. After a predetermined peak inspiratory pressure is reached, the inspiratory gas flow stops and the operator removes his or her finger from the exhalation port, thereby allowing the patient to exhale such that the exhaled gas flows out of the exhalation port and into the surrounding ambient atmosphere.

One example of such infant resuscitation system is commercially available as the NeoForce™ system from Flexicare, Inc., Irvine, California 92618.

In some instances, such as when the patient has or is suspected to have a respiratory infection, it may be desirable to filter microbes from the exhaled air before it is released into the surrounding ambient atmosphere. However, adding an external filtration device downstream of the exhalation port will typically result in an undesirable increase in the overall dead space within the circuit.

There exists a need in the art for the development of new resuscitation device and method wherein a T-piece circuit includes an internal microbial filtration system which reduces or eliminates microbial contamination from expired gas that exits through the exhalation port, without significantly increasing dead space within the T-piece circuit.

SUMMARY OF THE INVENTION

As used herein the term "other airway device" means a device that establishes a passageway for air into or out of the lungs; specifically, a device passed into the trachea by way of the mouth or nose or through an incision to maintain a clear respiratory passageway.

In general, the present invention provides a resuscitation circuit comprising; a tube having a proximal end and a distal end, the proximal end being connectable to a source of inspiratory gas; a distal tubular assembly having an upper arm, a side arm and a lower arm, the distal end of the tube being connected to the side arm of the distal tubular assembly; a mask or other patient airway device connected to the lower arm of the distal tubular assembly; and an exhalation port on the upper arm of the distal tubular assembly; the distal tubular assembly being configured such that blocking the exhalation port causes the inspiratory gas to flow through the mask or other patient airway device for delivery to a patient's lungs and, thereafter, unblocking the exhalation port allows respiratory gas exhaled into the mask or other patient airway device to exit through the exhalation port; wherein the T piece assembly further comprises a filter positioned upstream of the exhalation port, said filter being configured such that respiratory gas exhaled into the mask or other patient airway device must pass through the filter before exiting through the exhalation port. In some embodiments, the circuit may further comprise a positive end expiratory pressure (PEEP) valve. Such PEEP valve may be adjustable. In embodiments which include a PEEP valve, the PEEP valve may be attached to the circuit by any suitable means. For example, the PEEP valve may be attached to the filter by a conical connection interface, or it may comprise part of (e.g., be integrated or formed on or in) a filter housing, or it may be connected to the filter housing via a threaded connection or other suitable type of connection. In some embodiments, the exhalation port may be formed in a rotatable cap and, in embodiments which include a PEEP valve, rotation of said cap in a first direction may causes the PEEP valve to increase resistance to gas flow out of the exhalation port and rotation of the cap in a second direction causes the PEEP valve to decrease resistance to gas flow out of the exhalation port. In some embodiments, the filter may comprise a filter housing in which a quantity of filtration media is positioned. In some embodiments, such filter housing may comprise a lower housing portion and an upper housing portion configured such that, when attached to one another, the upper housing portion and lower housing portion form the housing, said housing having an interior space within which the filtration media is located and the filtration media may comprise a filter disc configured to fit within the interior space of the housing.

The present disclosure also includes a method for using a resuscitation circuit of the above-summarized character. Such method may comprise the steps of: connecting the proximal end of the tube to a source of inspiratory gas such that inspiratory gas is flows from the source, through the tube, through the side arm, through the upper arm and out of the exhalation port; engaging the mask or other patient airway with the patient; blocking the exhalation port, thereby causing the inspiratory gas to flow through the lower arm, through the mask or other patient airway device and into the patient's airway; and, thereafter, unblocking the exhalation port, thereby allowing exhaled air to pass from the patient's airway, through the mask or other patient airway device, through the lower arm, through the filter, through the upper arm and out of the exhalation port. In embodiments where the resuscitation circuit includes an adjustable PEEP valve, the method may further comprise the step of adjusting the amount of PEEP created by the PEEP valve. The source of inspiratory gas may comprise any suitable source of inspiratory gas, including but not limited to a resuscitator such as, for example, the NeoPIP™ Infant Resuscitator available commercially from Flexicare, Inc., Irvine, California 92618. Such resuscitator may be configured to deliver inspiratory gas (at which time the exhalation port may be blocked) until a predetermined inspiratory pressure or volume is reached, and may then interrupt or stop delivery of inspiratory gas (at which time the exhalation port may be unblocked), thereby allowing the patient to exhale with the exhaled air being passed through the filer before exiting the circuit.

BRIEF DESCRIPTION OF THE DRAWINGS

Non-limiting examples of the present invention are shown in the accompanying figures, as follows.

DETAILED DESCRIPTION OF EXAMPLES

The following detailed description and the accompanying drawings to which it refers are intended to describe some, but not necessarily all, examples or embodiments of presently disclosed systems and methods. The described examples or embodiments are to be considered in all respects only as illustrative and not restrictive. The contents of this detailed description and the accompanying drawings do not limit the scope of the invention in any way.

Figure 1:
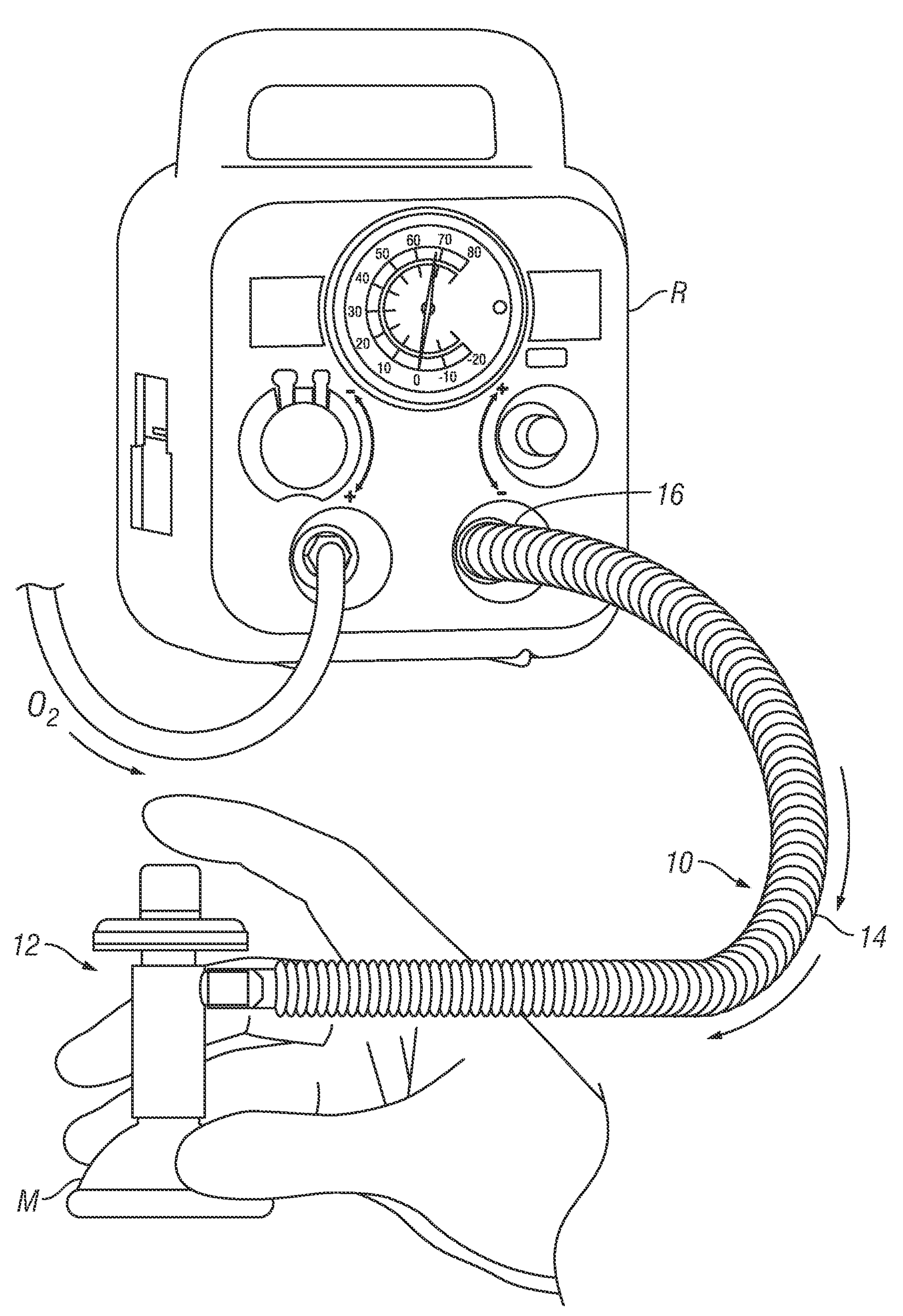
FIG. 1 is a diagram of one embodiment of a resuscitation system in accordance with the present disclosure.
Figure 2:
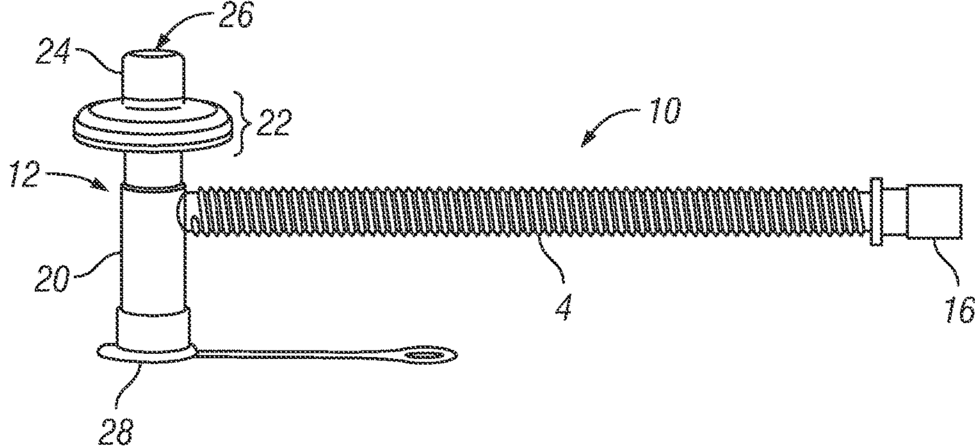
FIG. 2 is a side view of the T-piece circuit of the resuscitation system of FIG. 1.

FIG. 1 shows a resuscitation system which comprises a resuscitator device R, a T piece circuit 10 equipped with a filtration device, as described more fully below, and a mask. The resuscitator R may be a mechanical resuscitator device such as, for example, a NeoPIP™ Infant Resuscitator available commercially from Flexicare, Inc., Irvine, California 92618, or any other suitable apparatus for delivering a flow of inspiratory gas The mask M may be any suitable type of mask, such as, for example, a NeoForce™ Anatomical Mask or Round Mask (Size 0 or 1) available commercially from Flexicare, Inc., Irvine, California 92618.

In the example shown in the figures, the T piece circuit 10 comprises a tube 14, such as a length of corrugated ventilator tubing, having a connector 16 at one end and a distal tubular assembly, such as a T-piece assembly 12, at the other end. Although in this example the distal tubular assembly is shown to have a T configuration (i.e., a "T piece") it is to be appreciated that the distal tubular assembly may have other configurations, such as a Y or any other furcated or branched configuration having a first tubular arm, a second tubular arm and a third tubular arm. The connector 16 is configured for connecting the tube 14 to an outflow port of the resuscitator R.

Figure 3:
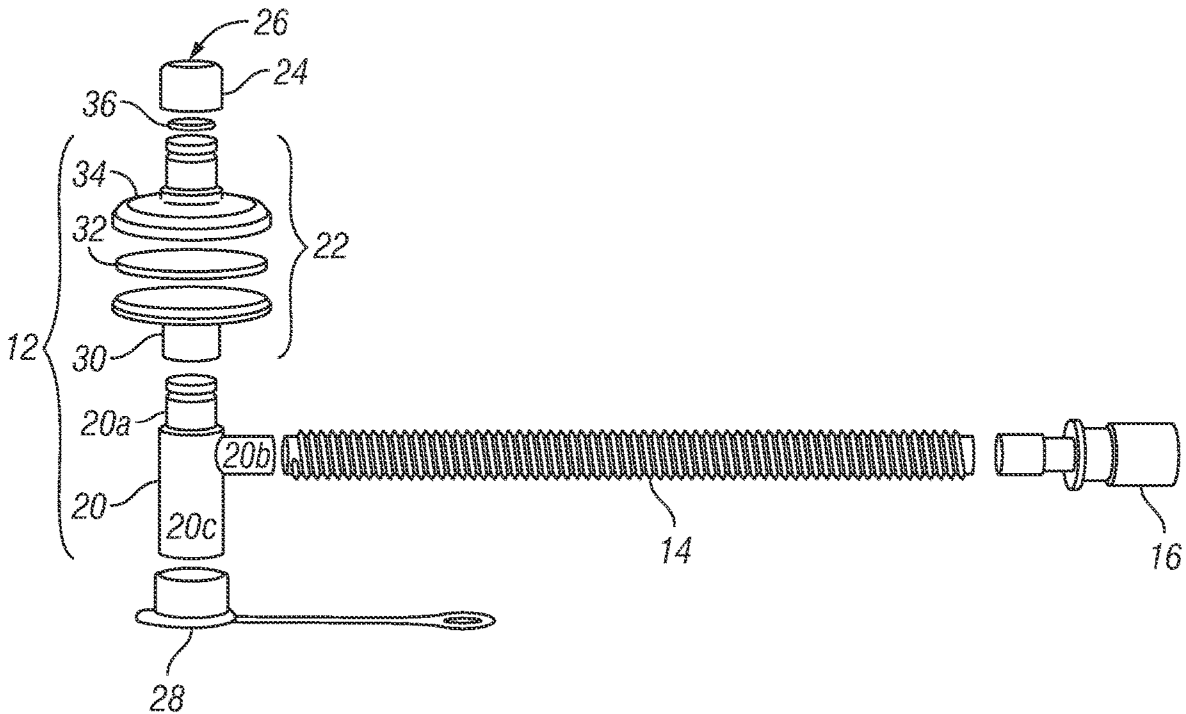
FIG. 3 is an exploded view of the T-piece circuit of FIG. 2.

As may be appreciated from the exploded view of FIG. 3, in this example, the T piece assembly 12 comprises a tubular T member 20 that has a first arm 20*a*, a second arm 20*b* and a third arm 20*c*, a filter sub-assembly 22 and an adjustable positive end expiratory pressure (PEEP) valve which comprises a rotatable PEEP valve cap 24 having an exhalation port 26 formed therein and a compressible O ring 36.

Prior to use, a safety cap 28 may be present on the opening of third arm 20*c* the tubular T member 20. At the time of use, that safety cap 28 is removed and a mask M or other airway-engaging device is attached to the third arm 20*c* of the tubular T member 20 in place of the safety cap 28, as shown in FIG. 1.

In the example shown, the filter sub-assembly 22 is connected to the first arm 20*a* of the tubular T member 20 and the distal end of the tube 14 is connected to the second arm 20*b*.

As seen in the exploded view of FIG. 3, the filter sub-assembly comprises a first housing portion 30 configured for attachment to the first arm 20*a* or the T piece 20, a filter disc 32 and an second housing portion 34. The filter disc 32 may comprise any suitable type of respiratory filtration media cut to fit snuggly within the interior space between the first and second housing portions 34, 30. The filter disc 32, may, for example, comprise a suitable filtration medium such as Separet 2402 (Freudenberg) which comprises a hydrophobic barrier and has high efficiency for filtration of microbes such as bacteria and viral particles. Viral filtration efficiency may be, for example, 99.99% or more. Alternatively, in some embodiments, an electrostatic filter material such as TechnoStat (Hollingsworth) may be used.

When assembled, the filter disc 32 may be initially welded ultrasonically or alternatively snap fit to the inner surface of the first housing portion. Then the second housing portion 34 is mounted on and ultrasonically welded to the first housing portion 30 such that the filter disc 32 is captured between the first housing portion 30 and second housing portion 32 and expired gasses which enter the first housing portion 30 will pass through the filter disc 32 before exiting though the second housing portion 34.

In some embodiments, the PEEP valve may function in the manner of a Tuohy Borst valve or similar arrangement whereby clockwise or counterclockwise rotation of the cap 24 causes more or less constriction of the channel through which exhaled air flows, thereby increasing or decreasing the PEEP. One non-limiting example is shown in FIG. 3, wherein a compressible or deformable member such as an O ring 36 may be mounted on the rim or gas exit port of the second housing portion and rotatable PEEP valve cap 24 may be attached to the filter assembly as a distinct component by a conical connection interface as per ISO 5356-1 or other suitable connection. Alternately, the PEEP valve may be constructed as part of the filter housing 34 or may be attached by a threaded or other attachment.

In the example shown in FIG. 3, as the PEEP valve cap 24 is rotated in one direction, it screws downwardly thereby compressing the O ring 36, such that the diameter of the O ring's opening decreases, thereby increasing resistance to gas flow out of the exhalation port 26. As the PEEP valve cap 24 is rotated in the opposite direction, it screws upwardly thereby decompressing the O ring 36 such that the diameter of its center opening increases and resistance to gas flow out of the exhalation port 26 is diminished.

Figure 4:
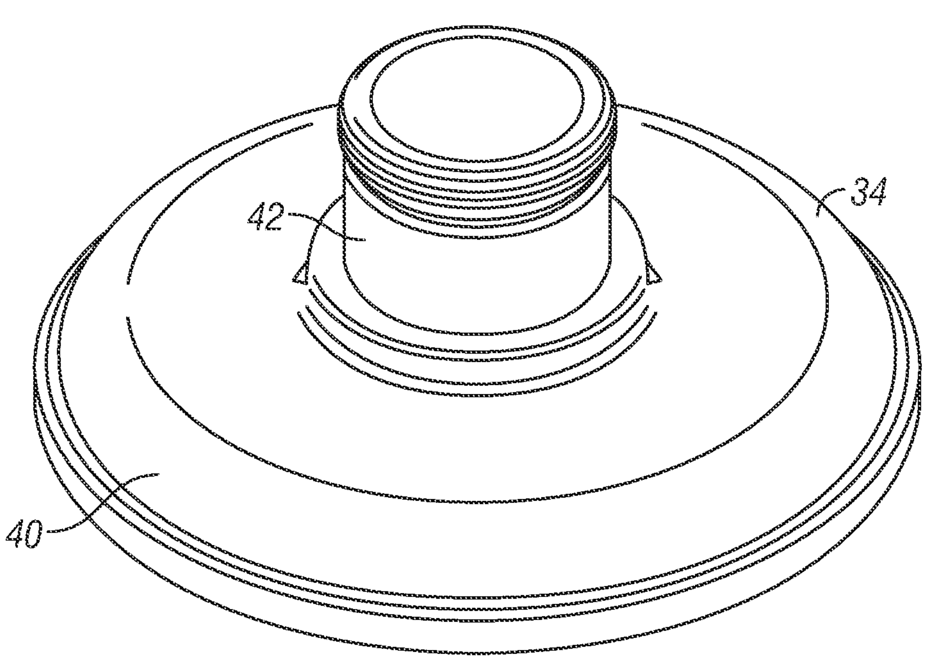
FIG. 4 is a perspective view of an embodiment of the first housing portion of the filter assembly of the resuscitation system, which does not require an O ring.
Figure 5:
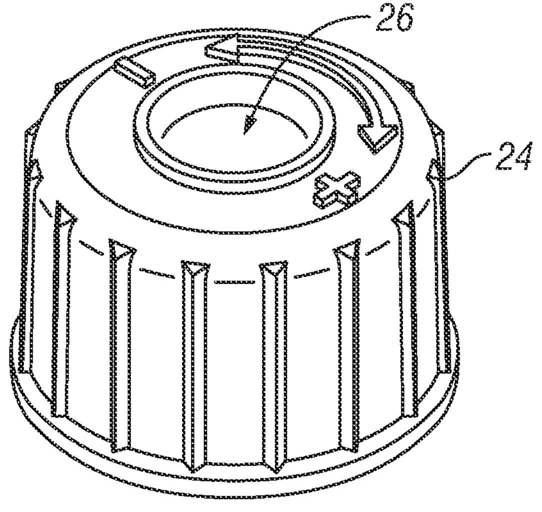
FIG. 5 is a perspective view of a PEEP valve cap useable with the embodiment shown in FIGS. 4 through 4B.
Figure 5A:
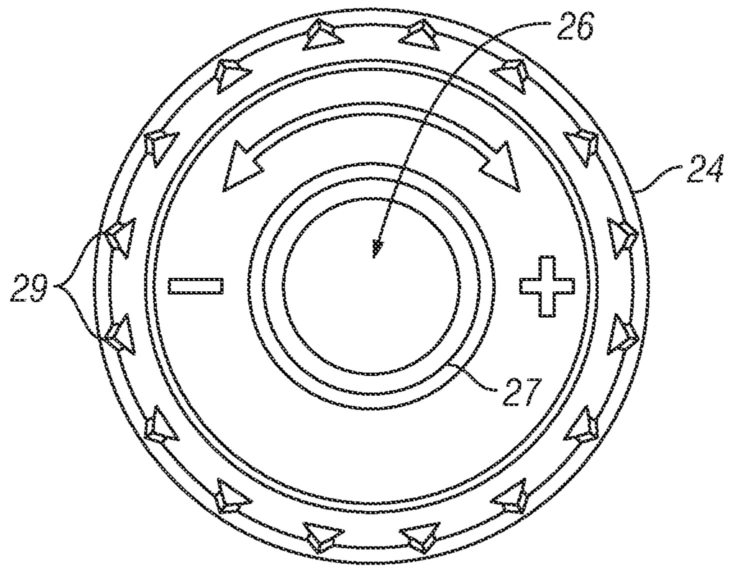
FIG. 5A is a bottom view of the PEEP valve cap shown in FIG. 5.
Figure 5B:
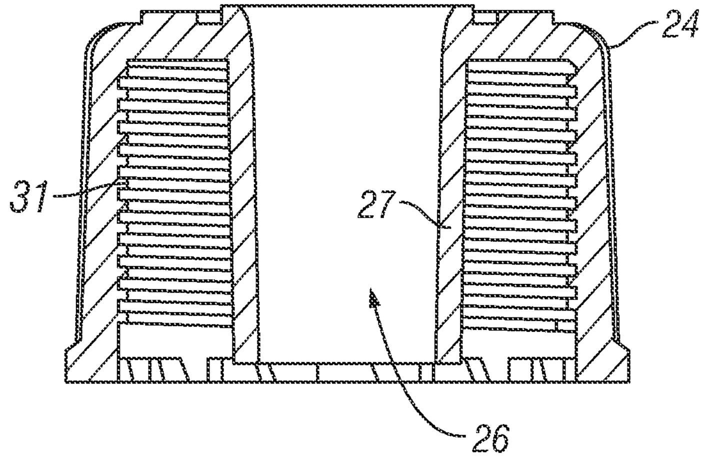
FIG. 5B is a side cross-sectional view of the PEEP valve cap shown in FIG. 5.

An alternative example of a PEEP valve assembly, which does not employ an O ring, is shown in FIGS. 4 through 5B. In this alternative, a flow-restricting cone 52 having a central flow aperture 54 is mounted within a cylindrical upper body portion 42 of the second housing portion 34. The flow aperture 54 of the cone 52 defines the maximum settable PEEP for a given flow. The cone 52 is mounted on a round support member 56, which is attached to the lower body portion 40 of the second housing portion 34. Alternate outflow apertures 58 are formed in the support member 52 to provide an alternate flow path outside the cone 52. The PEEP valve cap 24 shown in FIGS. 5 through 5B has internal threads 31 which correspond to external threads 44 on the upper body portion 42 of the second housing portion 34. Thus, the PEEP valve cap 24 may be alternately screwed downwardly and upwardly on the upper body portion 42 of the second housing portion 34. An obturator member 27, which has a hollow flow passage 26, extends downwardly within the PEEP valve cap 24. As the PEEP valve cap 24 is screwed downwardly, the cone 52 protrudes further into the hollow flow passage 26 of the obturator member 27 thereby progressively decreasing the space between the outer surface of the cone 52 and wall of the obturator member 27 and allowing a progressively smaller portion of the expired respiratory gas to escape through the alternate outflow apertures 58. This causes the PEEP. The maximum PEEP is reached when the PEEP valve cap 24 is screwed down to its furthest extent, which blocks all or substantially all outflow of expired respiratory gas through the alternate outflow apertures 58 and requires all or substantially all of the expired respiratory gas to pass through the hollow interior of the cone 52 and out of its central outflow aperture 54. In this regard, a seal or O ring may be provided on the outside of the filter housing to ensure that the sole path of the gas is through the PEEP valve cap 24.

Conversely, as the PEEP valve cap 24 is unscrewed (upwardly), the obturator member 27 rises and a progressively greater portion of the expired respiratory gas is allowed to escape through the alternate flow apertures 58. In this manner, PEEP may be adjusted to suit the clinical need by screwing or unscrewing the PEEP valve cap 24.

Figure 4A:
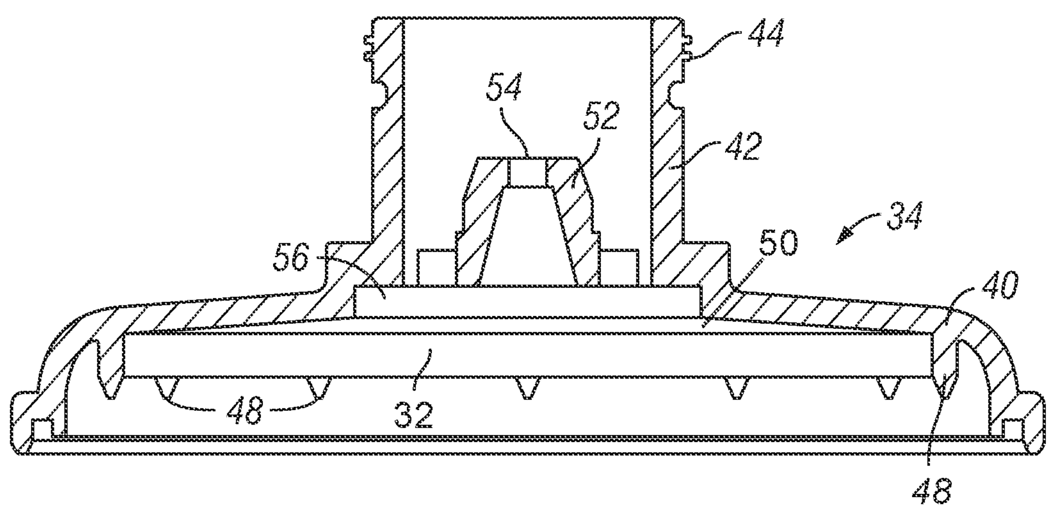
FIG. 4A is a cross-sectional view of the alternative embodiment of the first portion of the filter assembly shown in FIG. 4.
Figure 4B:
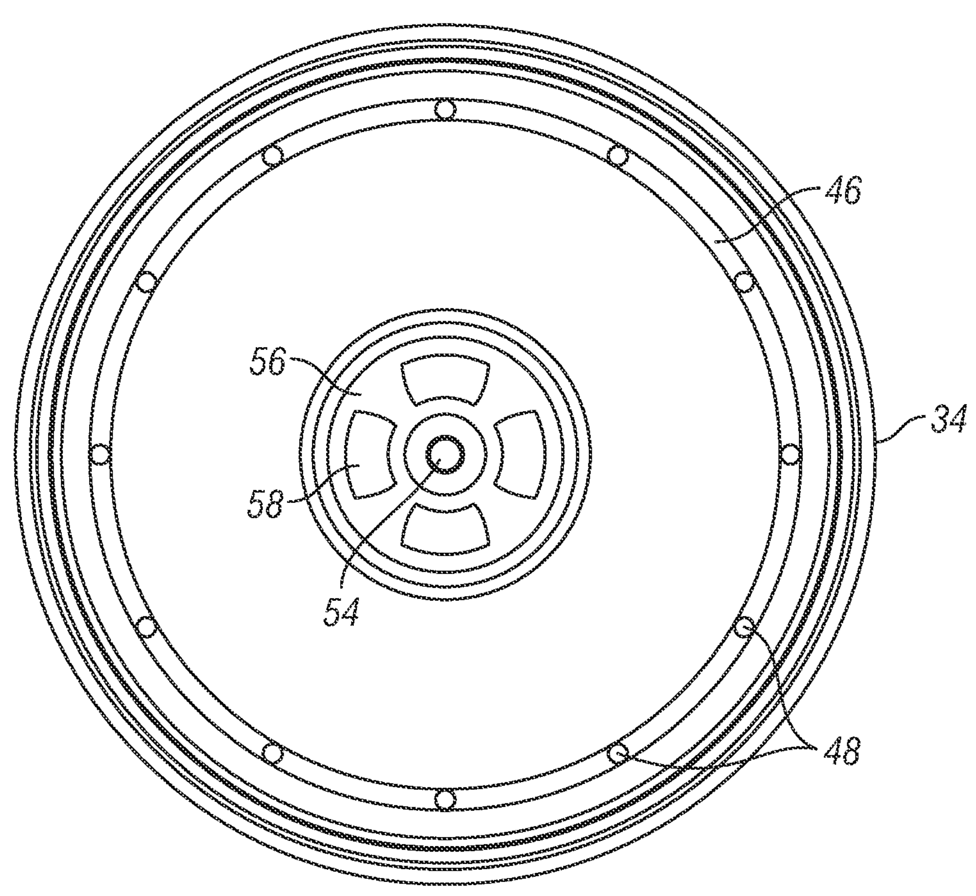
FIG. 4B is a bottom view of the alternative embodiment of the first portion of the filter assembly shown in FIG. 4.

In many embodiments, it will be important to ensure that the filter disc 32 performs its filtration function without substantially impeding or blocking outflow of expired respiratory gas. This may be accomplished by mounting the filter disc 32 such that sufficient surface area on both sides of the filter disc 32 remains open, unobstructed and available for passage/filtration of outflowing expired area. In the example seen in FIG. 4A, the filter disc 32 is constructed and fits within the interior of the housing assembly 12 such that a plenum or cavity exists adjacent to most of the lower (inflow) side of the filter disc 32 and another plenum or cavity 50 exists adjacent to most of the upper (outflow) side of the filter disc. The filter disc 32 firmly snap fits within, and is held in its operative position by, filter-engaging members 48. When in its operative position, only a perimeter region of the filter disc 32 contacts the filter-engaging members 48 and/or inner surface of the lower body portion 40 of the second housing portion 34. Thus, the entire bottom (inflow) surface of the filter disc 32 remains exposed to, and able to receive expired respiratory gas from, a plenum or open space within the housing below the filter disc 32. Also, most of the upper surface of the filter disc 32 remains exposed to, and able to deliver filtered gas into, a plenum or space 50 located between the upper (outflow) surface of the filter disc 32 and the wall of the lower body portion 40 and/or solid portions of the support member 56. Additionally, the filter disc 32 may be constructed so that it does not deform or bow upwardly in any manner that would substantially decrease the size of the air plenum or space 50 and/or otherwise cause the upper surface of the filter disc 32 to press against or contact the wall of the lower body portion 40 or solid portions of the support member 50 in any manner that would prevent the filter disc 32 from adequately performing its filtration function. In this regard, it is to be appreciated that the filter surface area that must remain unobstructed to permit the filtration function of the filter(s) my vary depending on the design, size and flow characteristics of components of the filter assembly 12. Thus, in different embodiments, the components may be constructed so that during operation all, substantially all, more than half, at least 95%, at least 90%, at least 85%, at least 80%, at least 75%, at least 70%, at least 65%, at least 60% or at least 55% of the upper (outflow) and lower (inflow) surfaces of the filter disc 32 remain unobstructed and open to air flow.

Although the figures show a round filter disc 32 it is to be appreciated that filters of various other sizes and/or shapes may be used, and in some embodiments more than one filter may be used.

The system described above may be set up and used as follows:

A. the connector 16 is connected to the outlet of resuscitator R;

B. the resuscitator R and any associated $O_2$ blender is/are initialized and adjusted so that the resuscitator R is delivering the desired inspiratory gas (air, oxygen or blended air/oxygen mixture) at the desired flow rate through the T piece circuit 10;

C. with the cap 28 remaining in place on the third arm 20*c* of the tubular T member 20, repeatedly place finger firmly on the exhalation port 26 while adjusting peak inspiratory pressure setting on the resuscitator R and PEEP setting by rotating or counter-rotating PEEP valve cap 24;

D. remove cap 28 and attached mask M to third arm 20*c* of T-piece assembly;

E. place mask M over the patient's mouth and nose;

F. place finger over exhalation port 26 to block flow out of exhalation port 26 and deliver inspiratory breath through mask M;

G. following delivery of the inspiratory breath, remove finger from exhalation port to allow exhalation through upstream filter disc 32 and out of exhalation port.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. In addition, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A resuscitation circuit comprising:

a tube having a proximal end and a distal end, the proximal end being connectable to a source of inspiratory gas;

a distal tubular assembly having a first arm, a second arm and a third arm, the distal end of the tube being connected to the second arm of the distal tubular assembly;

a mask or other patient airway device connected to the third arm of the distal tubular assembly; and an exhalation port on the first arm of the distal tubular assembly;

wherein;

the distal tubular assembly is configured such that blocking the exhalation port causes the inspiratory gas to flow through the mask or other patient airway device for delivery of respiratory gas to a patient's lungs and, thereafter, unblocking the exhalation port allows respiratory gas that is exhaled into the mask or other patient airway device to exit through the exhalation port;

the distal tubular assembly further comprises a filter positioned in a filter housing upstream of the exhalation port, said filter being configured such that respiratory gas exhaled into the mask or other patient airway device must pass through the filter before exiting through the exhalation port; and an adjustable positive end expiratory pressure (PEEP) valve is connected to the filter housing via a threaded connection.

2. A resuscitation circuit according to claim 1 wherein the PEEP valve comprises a rotatable PEEP valve cap, and the exhalation port is formed in said rotatable PEEP valve cap, and wherein rotation of said PEEP valve cap in a first direction causes an increase in resistance to gas flow out of the exhalation port and rotation of the PEEP valve cap in a second direction causes a decrease in resistance to gas flow out of the exhalation port.

3. A resuscitation circuit according to claim 1 wherein the filter comprises a quantity of filtration media positioned within the filter housing.

4. A resuscitation circuit according to claim 3 wherein the filter housing comprises a first housing portion and a second housing portion configured such that, when attached to one another, the first housing portion and second housing portion form the filter housing, said filter housing having an interior space within which the filter is located.

5. A resuscitation circuit according to claim 4 wherein the filter is configured to fit within the interior space of the filter housing.

6. A resuscitation circuit according to claim 5 wherein the filter is constructed and fits within the interior of the filter housing such that a plenum or space exists adjacent to most of an inflow side of the filter and another plenum or space exists adjacent to most of an outflow side of the filter.

7. A resuscitation circuit according to claim 1 wherein the filter is capable of filtering viral particles from exhaled gas.

8. A method for resuscitation of a patient, said method comprising the steps of:

obtaining or providing a resuscitation circuit which comprises;

a tube having a proximal end and a distal end, the proximal end being connectable to a source of inspiratory gas;

a distal tubular assembly having a first arm, a second arm and a third arm, the distal end of the tube being connected to the second arm of the distal tubular assembly;

a mask or other patient airway device connected to the third arm of the distal tubular assembly; and an exhalation port on the first arm of the distal tubular assembly;

the distal tubular assembly being configured such that blocking the exhalation port causes the inspiratory gas to flow through the mask or other patient airway device for delivery to a patient's lungs and, thereafter, unblocking the exhalation port allows respiratory gas exhaled into the mask or other patient airway device to exit through the exhalation port;

wherein the distal tubular assembly further comprises a filter positioned upstream of the exhalation port, said filter being configured such that respiratory gas exhaled into the mask or other patient airway device must pass through the filter before exiting through the exhalation port connecting the proximal end of the tube to a source of inspiratory gas such that inspiratory gas is flows from the source, through the tube, through the second arm, through the first arm and out of the exhalation port;

engaging the mask or other patient airway with the patient;

blocking the exhalation port, thereby causing the inspiratory gas to flow through the third arm, through the mask or other patient airway device, and into the patient's airway; and, thereafter, unblocking the exhalation port, thereby allowing exhaled air to pass from the patient's airway, through the mask or other patient airway device, through the third arm, through the filter, through the first arm and out of the exhalation port.

9. A method according to claim 8 wherein the resuscitation circuit includes an adjustable PEEP valve and wherein the method further comprises the step of:

adjusting an amount of PEEP created by the PEEP valve.

10. A method according to claim 8 wherein the source of inspiratory gas comprises a resuscitator.

11. A method according to claim 10 wherein the resuscitator delivers said inspiratory gas during the blocking step and ceases to deliver said inspiratory gas during the unblocking step.

12. A method according to claim 11 wherein the resuscitator delivers the inspiratory gas until a predetermined inspiratory pressure or volume is reached, at which time the resuscitator stops delivery of the inspiratory gas and, thereafter, the unblocking step is performed.

* * * * *